United States Patent [19]

Astoin et al.

[11] Patent Number: 4,745,125
[45] Date of Patent: May 17, 1988

[54] ANTIULCER BENZIMIDAZOLES

[75] Inventors: Jacques N. Astoin; Bernard Hublot, both of Paris; Francis Lepage, Creteil, all of France

[73] Assignee: Novapharme, Paris, France

[21] Appl. No.: 4,607

[22] Filed: Jan. 20, 1987

[30] Foreign Application Priority Data

Jan. 20, 1986 [FR] France .................. 86 00691

[51] Int. Cl.$^4$ ............... A61K 31/415; C07D 405/06; C07D 235/30
[52] U.S. Cl. .................. 514/388; 514/338; 546/278; 548/306
[58] Field of Search ........ 548/306; 546/271; 514/338, 388

[56] References Cited

U.S. PATENT DOCUMENTS 4,463,181 7/1984 Morwick et al. ............ 548/306

FOREIGN PATENT DOCUMENTS 0015339 9/1980 European Pat. Off. ......... 548/306
0111993 6/1984 European Pat. Off. ......... 548/306
2374311 7/1978 France .................. 548/306

OTHER PUBLICATIONS

*Chemical Abstracts,* 101:54993y, (1984) [Graubaum, H., et al., *Z. Chem.* 1984, 24(2), 57–58].
*Chemical Abstracts,* 82:165889c, (1975) [Japan Kokai, 75 06, 722, Yoshida et al., 1/23/75].
Hofmann, K., *Imidazole and Its Derivatives,* Part I, Interscience, New York, 1953, pp. 273–274.

*Primary Examiner*—Richard A. Schwartz
*Attorney, Agent, or Firm*—Wegner & Bretschneider

[57] ABSTRACT

Antiulcer amino-benzimidazole compounds substituted on the nitrogen; these compounds correspond to the following general formula:

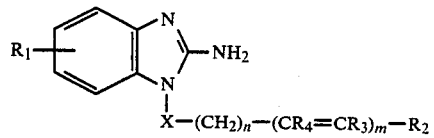

in which the various substituents are defined hereinbelow.

10 Claims, No Drawings

ANTIULCER BENZIMIDAZOLES

The object of the present invention is a group of new amino-benzimidazole compounds substituted on the nitrogen, a process for preparing them and the therapeutic application thereof.

The compounds of the invention correspond to the following general formula:

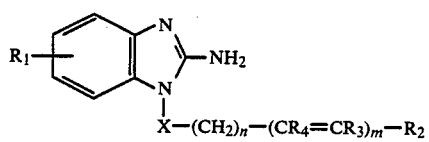

(I)

in which:
x represents a carbonyl or sulfonyl radical;
$R_1$ represents a hydrogen atom, a halogen atom, particularly chlorine, or an alkoxy radical, particularly methoxy;
$R_2$ represents a hydrogen atom, an alkyl radical, phenyl or a nitrogen or oxygen heterocyclic radical, possibly substituted;
$R_3$ and $R_4$ represent each independent of the other, a hydrogen atom or an alkyl radical;
n is less than or equal to 10 and more particularly equal to 0, 1 or 2;
m is equal to 0, 1 or 2 with the restriction that m and n not be simultaneously equal to zero.

It is preferable that n be equal to 0 and m equal to 1 or 2.

The invention equally concerns the addition salts formed on the amines using physiologically acceptable acids, such as hydrochloric acid, hydrobromic acid, phosphoric acid, sulfuric acid, oxalic acid, lactic acid, tartric acid, acetic acid, salicylic acid, benzoic acid, citric acid, ascorbic acid, adipic acid, and naphthalenedisulfonic acid.

The compounds of the invention may be prepared from 2-amino benzimidazoles of the formula:

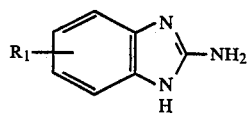

(II)

in which $R_1$ has the meaning given above
which is reacted with an acid chloride of the formula:

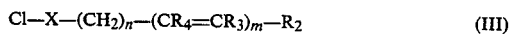

Cl—X—(CH$_2$)$_n$—(CR$_4$=CR$_3$)$_m$—R$_2$          (III)

in which $R_2$, $R_3$, $R_4$ m and n have the meanings given above,
in an aprotic solvent at a temperature of between $-60°$ C. and $+20°$ C. and in the presence of a weak base.

Particularly appreciated as aprotic solvents are acetone, benzene, dioxane or tetrahydrofuran.

The weak base may be a bicarbonate of an alkaline metal, for example of sodium (NaHCO$_3$), or triethylamine.

The compounds of the invention, according to trials which have been carried out, present an interesting antiulcer activity rendering them apt to the treatment of gastric and duodenal ulcers.

The following examples illustrate the preparation of some of the compounds of the invention. The chemical analyses and IR and RMN spectra establish the structure of these compounds.

EXAMPLE 1

1-(2,4 hexadienoyl) 2-amino benzimidazole

A solution of 2-amino benzimidazole (4 g, or 0.030 mole) and triethylamine (4.2 ml, or 0,029 mole) in 70 ml of anhydrous tetrahydrofuran, is chilled to a temperature of between $-5°$ and $0°$ C. To this solution is slowly added 4 g (0.030 mole) chloride of 2,4 hexadienoic acid in solution in 50 ml of anhydrous tetrahydrofuran. After being agitated, the mixture is left to return to ambiant temperature, after which it is poured into water. The precipitate is drained and washed with water. After recrystallization in toluene, 4.12 g (60% yield) is obtained of a crystallized compound having a melting point of 215° C. and the following structure (90% purity):

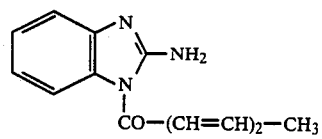

EXAMPLE 2

1-hexanoyl 2-amino benzimidazole

A solution of 2-amino benzimidazole (8 g, or 0.060 mole) and triethylamine (10 g, or 0,099 mole) in 150 ml of anhydrous acetone, is chilled to a temperature of $-65°$ C. under nitrogen. To this solution is added 12.1 g (0.09 mole) hexanoyl chloride in solution in 150 ml of anhydrous acetone at a temperature of $-60°$ C. After the mixture has been agitated at this temperature for around 1 hour, 100 ml of water is added to it, at a temperature of between $-30°$ and $-20°$ C., after which it is all poured into 500 ml of water. The precipitate is filtered, and dried in a dessicator. After purification, 7 g (50.5% yield) is obtained of a crystallized compound having a melting point of 200° C. and the following structure (90% purity):

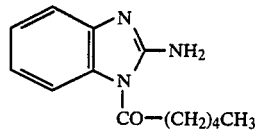

EXAMPLE 3

1-(2-phenyl ethenylsulfonyl) 2-amino benzimidazole

A solution of 2-amino benzimidazole (2.53 g, or 0.019 mole) and triethylamine (2.1 g, or 0,021 mole) in 100 ml of anhydrous benzene, is chilled to a temperature of 10° C. under an atmosphere of dry nitrogen. To this solution is added drop-by-drop over 20 minutes, a solution of 5 g (0.02 mole) 2-phenyl ethenyl-sulfonlyl chloride in 50 ml of anhydrous benzene. The reaction mixture is left to rest for around an hour at a temperature less than, or equal to 10° C., after which it is allowed to return to ambiant temperature and agitated for 18 hours. The reaction mixture is poured into water: the precipitate is separated by filtration and washed with cyclohexane.

After purification by column chromatography (WOELM 63-200 silicagel; chloroform eluant), 3 g (53% yield) is obtained of a crystallized compound having a melting point of 191° C. and the following structure (90% purity):

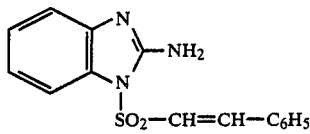

As indicated above, the compounds of the invention have been submitted to trials which have demonstrated their anti-ulcer activity.

The pharmacological assays rest principally on the ulcer technique of SHAY (Gastro-enterology, 1945, 15, 43) accompanied by an evaluation of the results according to the method of KEYRILAINEN and PAASONEN (Acta Pharmacol. and Toxicol., 1957, 13, 22). We will briefly describe this technique.

Male Sprague-Dawley rates weighing 200 to 240 g are kept in individual cages with water provided at will. Then their pylorus was ligatured under ether anesthetic. The animals are then re-placed in their cage, watered and sacrificed 17 hours later.

The substances under study are administered orally 3 times: at 48 and 24 hours prior to ligature, and immediately after. The group of control rats are only given a solution of sodium carboxymethyl cellulose (CMC) or distilled water according to the solubility in water of the studied product.

The rat's stomach is cut open along the large curve, washed and spread out on a sheet of cork for examination.

The number of ulcers are counted and their qualities evaluated according to the criteria of KEYRILAINEN and PAASONEN who attribute a value of 1 to small ulcers of from 0 to 2 mm, a value of 5 for medium-sized ones of 2 to 5 mm, a value of 10 for large ulcers of from 5 to 10 mm, and 20 for those larger than 10 mm and for perforations.

The ulcer index, UIp, for a given substance, p, is defined as the quotient of the sum of the attributed values for all the ulcers observed per number of animals. The anti-ulcer activity, Δp, of a studied substance, p, is defined by the relative variation, expressed as a %, of the ulcer index of the studied product relative to the ulcer index for the control group, c, that is, by the formula:

$$\Delta p = \frac{UI\,p - UI\,c}{UI\,c} \times 100$$

in which:

Δp is expressed as a %
UI p is the ulcer index of the substance studied
UI c is the ulcer index of the control group.

The toxicity of the substances (lethal dose) is equally measured.

The results obtained for the compounds of the invention are shown in the tables (I and II) further on.

In addition, cimetidine, a substance widely used in the treatment of gastric and duodenal ulcers, has been used as a reference and submitted to the same pharmacological assays at a dose of three times 100 mg/kg. The result of its anti-ulcer activity is 86% for a DL50 of 2120 mg/kg.

TABLE I

Anti-ulcer activity of compounds of the invention having the formula:

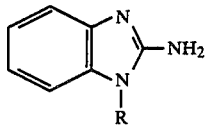

in which R represents: X—(CH$_2$)$_n$—(CR$_4$=CR$_3$)$_m$ R$_2$; the symbols X, R$_2$, R$_3$, R$_4$, m and n have the meanings previously given.

| REFERENCE | NATURE OF R | MELTING POINT (°C.) | DOSE ADMINISTERED p.o. (mg/kg) | ANTI-ULCER ACTIVITY Δ(%) | TOXICITY p.o. (mg/kg) |
|---|---|---|---|---|---|
| 2453 | CO—(CH$_2$)$_4$—CH$_3$ | 200 | 200 × 3 | 45 | DL$_{50}$ = 2000 |
| 2452 | CO—(CH$_2$)$_6$—CH$_3$ | 123 | 200 × 3 | 43 | DL$_0$ ≧ 2000 |
| 2211 | CO—CH=C(CH$_3$)$_2$ | 160 | 200 × 3 | 62 | DL$_0$ ≧ 2000 |
| 2474 | CO—CH=CH—C$_6$H$_5$ | 186 | 200 × 3 | 43 | DL$_0$ ≧ 2000 |
| 2340 | CO—CH=CH—C$_6$H$_4$—OCH$_3$ | 220 | 200 × 3 | 45 | DL$_0$ ≧ 2000 |

TABLE I-continued

Anti-ulcer activity of compounds of the invention having the formula:

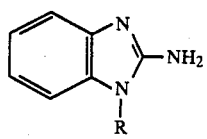

in which R represents: X—(CH$_2$)$_n$—(CR$_4$=CR$_3$)$_m$ R$_2$; the symbols X, R$_2$, R$_3$, R$_4$, m and n have the meanings previously given.

| REFERENCE | NATURE OF R | MELTING POINT (°C.) | DOSE ADMINISTERED p.o. (mg/kg) | ANTI-ULCER ACTIVITY Δ(%) | TOXICITY p.o. (mg/kg) |
|---|---|---|---|---|---|
| 2355 | CO—CH=CH—C$_6$H$_2$(OCH$_3$)$_3$ | 117 | 200 × 3 | 65 | DL$_0$ ≧ 2000 |
| 2368 | CO—CH=C(CH$_3$)—cyclohexenyl | 181 | 200 × 3 | 49 | DL$_0$ ≧ 2000 |
| 2475 | CO—C(CH$_3$)=CH—C$_6$H$_5$ | 168 | — | — | DL$_0$ ≧ 2000 |
| 2407 | CO—CH=CH—(5-methylfuran-2-yl) | 211 | 200 × 3 | 64 | DL$_0$ ≧ 2000 |
| 2433 | CO—CH=CH—(pyridin-3-yl) | 208 | 200 × 3 | 51 | DL$_0$ ≧ 2000 |
| 2455 | CO—CH$_2$=CH=CH$_2$ | 167 | — | — | DL$_0$ ≧ 2000 |
| 2454 | CO—CH$_2$—CH=CH—CH$_2$—CH$_3$ | 197 | — | — | DL$_0$ ≧ 2000 |
| 2379 | CO—(CH=CH)$_2$—H | 172 | 50 × 3 | 63 | DL$_{50}$ ≧ 2000 |
| 2170 | CO—(CH=CH)$_2$—CH$_3$ | 215 | 100 × 3 | 93 | DL$_0$ = 2000 |
| 2356 | CO—(CH=CH)$_2$—C$_6$H$_5$ | 221 | 200 × 3 | 0 | DL$_0$ ≧ 2000 |
| 2434 | CO—(CH$_2$)$_2$—CH=CH$_2$ | 148 | 200 × 3 | 68 | DL$_{20}$ = 2000 |
| 2133 | CO—(CH$_2$)$_8$—CH=CH$_2$ | 145 | 200 × 3 | 47 | DL$_0$ ≧ 2000 |
| 2432 | SO$_2$CH=CH—C$_6$H$_5$ | 191 | 200 × 3 | 26 | DL$_0$ ≧ 2000 |

TABLE II

Anti-ulcer activity of compounds according to the invention substituted by a chloro or methoxy radical on the 4, 5, 6 or 7 position

| REFERENCE | CHEMICAL FORMULA OF THE SUBSTANCE STUDIED | MELTING POINT (°C.) | DOSE ADMINISTERED p.o. (mg/kg) | ANTI-ULCER ACTIVITY Δ(%) | TOXICITY p.o. (mg/kg) |
|---|---|---|---|---|---|
| 2381 | (benzimidazole with OCH₃, NH₂, CO(CH=CH)₂—CH₃) | ca. 250 | 200 × 3 | 0 | $DL_0 \geq 2000$ |
| 2380 | (benzimidazole with Cl, NH₂, CO(CH=CH)₂—CH₃) | ≧ 198 | 200 × 3 | 50 | $DL_0 \geq 2000$ |
| 2451 | (benzimidazole with Cl, NH₂, COCH=CH-furanyl) | ≧ 195 | 200 × 3 | 31 | $DL_0 \geq 2000$ |

The tables above show that the compounds of the invention possess for the most part an interesting anti-ulcer activity and that their toxicity is in general low.

Four of these compounds:
1-[3,4,5-trimethoxy-phenyl) propenoyl] 2-amino benzimidazole (Ref. 2355);
1-(4-pentenoyl) 2-amino benzimidazole (Ref. 2434);
1-[3-(2-furanyl) propenoyl] 2-amino benzimidazole (Ref. 2407); and
1-(2,4-hexadienoyl) 2-amino benzimidazole (Ref. 2170), have an anti-ulcer activity equal to or greater than 65% for a weah toxicity.

Among them, the 1-(2,4-hexadienoyl) 2-amino benzimidazole offers, for an active dose of 100 mg/kg, an anti-ulcer activity Δ of 93% for a $DL_0$ greater than 2000 mg/kg, i.e. 20 times the active dose. Under experimental conditions similar to those applied to cimetidine, this compound thus possesses an anti-ulcer activity comparable to that of cimetidine with less toxicity.

The compounds of the invention thus represent a new class of medicines able to be used in the treatment of gastric and duodenal ulcers in association with pharmaceutically acceptable vehicles or excipients. The dosage orally, in pills, tablets or dragées will be around 200 to 1500 mg/kg per day, administered in three times, for example.

We claim:

1. A compound which is a derivative of benzimidazole corresponding to the following formula:

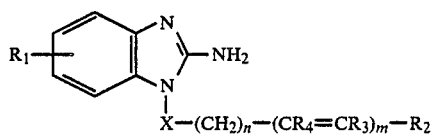

wherein
X represents a carbonyl or sulfonyl radical;
$R_1$ represents a hydrogen atom, a halogen atom, or a methoxy radical;
$R_2$ represents a hydrogen atom, a methyl or ethyl radical, or a phenyl, pyridyl or furanyl radical, possibly substituted;
$R_3$ and $R_4$ represent, each independent of the other, a hydrogen atom or an alkyl radical;
n is less than or equal to 10; and
m is equal to 1 or 2
or a physiologically acceptable acid salt thereof.

2. The compound of claim 1 wherein n is equal to 0, 1 or 2.

3. The compound of claim 1 wherein n is equal to 0.

4. A pharmaceutical composition for the treatment of ulcers which comprises a therapeutically effective amount of a compound of the formula:

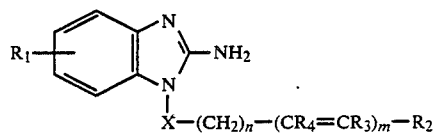

wherein
X represents a carbonyl or sulfonyl radical;
$R_1$ represents a hydrogen atom, a halogen atom, or a methoxy radical;
$R_2$ represents a hydrogen atom, a methyl or ethyl radical, or a phenyl, pyridyl or furanyl radical, possibly substituted;
$R_3$ and $R_4$ represent, each independent of the other, a hydrogen atom or an alkyl radical;
n is less than or equal to 10; and
m is equal to 1 to 2
or a physiologically acceptable acid salt thereof, and a pharmaceutically acceptable carrier.

5. The pharmaceutical composition of claim 4 wherein n is equal to 0, 1 or 2.

6. The pharmaceutical composition of claim 4 wherein n is equal to 0.

7. The pharmaceutical composition of claim 4 wherein the compound is selected from the group consisting of 1-[3-(3,4,5-trimethoxy-phenyl) propenoyl]

2-amino benzimidazole, 1-(4-pentenoyl) 2-amino benzimidazole, 1-[3-(2-furanyl) propenoyl] 2-amino benzimidazole, and 1-(2,4-hexadienoyl) 2-amino benzimidazole.

8. The pharmaceutical composition of claim 4 wherein the compound is 1-(2,4-hexadienoyl) 2-amino benzimidazole.

9. A method of treating ulcers in a patient which comprises administering to said patient a therapeutically effective amount of the compound of claim 1.

10. The method of claim 9 wherein the compound is orally administered at a dosage from about 200 to about 1500 mg/kg per day.

* * * * *